United States Patent [19]

Kondo

[11] Patent Number: 4,832,948
[45] Date of Patent: May 23, 1989

[54] PERMANENT WAVE SOLUTION

[76] Inventor: Tokuzo Kondo, 3F. Fujiya Bldg., 6-5 Ginza 2-chome, Chuo-ku, Tokyo, Japan

[21] Appl. No.: 140,945

[22] Filed: Dec. 28, 1987

Related U.S. Application Data

[63] Continuation of Ser. No. 897,432, Aug. 18, 1986, abandoned.

[30] Foreign Application Priority Data

Sep. 10, 1985 [JP] Japan .................................. 60-200233

[51] Int. Cl.$^4$ ................................................ A61K 7/09
[52] U.S. Cl. ................................................ 424/72
[58] Field of Search ........................................ 424/72

[56] References Cited

U.S. PATENT DOCUMENTS

| | | | |
|---|---|---|---|
| 2,631,965 | 3/1953 | Schnell | 424/72 |
| 3,025,218 | 3/1962 | Strain et al. | 424/72 |
| 3,148,126 | 9/1964 | Martin | 424/72 |
| 4,192,863 | 3/1980 | Kondo | 424/72 |

*Primary Examiner*—Douglas W. Robinson
*Assistant Examiner*—Zohreh Fay
*Attorney, Agent, or Firm*—Armstrong, Nikaido, Marmelstein, Kubovcik & Murray

[57] ABSTRACT

A novel one-step permanent wave solution capable of providing permanently waved curls with a durability of six months or more without damaging hair by decomposition of cystine. The permanent wave solution consists of (by weight):

thioglycolic acid: 2.5 to 3.5%;
28% ammonia water: 1.0 to 4.0%;
caustic soda or caustic potash: 0.045 to 0.075%;
monoethanolamine, diethanolamine, or triethanolamine: 0.03 to 0.06%;
tartaric acid or citric acid: 0.1 to 0.2%;
ethyl alcohol: 0.6 to 3.0%; and
distilled water: the remainder, alkalinity (the quantity, in terms of ml., of 0.1N-HCl which is required for neutralizing 1 ml. of the solution) of the above solution being adjusted to not more than 3.0.

3 Claims, No Drawings

PERMANENT WAVE SOLUTION

This application is a continuation of application Ser. No. 897,432 filed Aug. 18, 1986, now abandoned.

BACKGROUND OF THE INVENTION

1. Field of the Invention

The present invention relates to an improvement in a one-step permanent wave solution.

2. State of the Art

Among permanent wave solutions heretofore known, wave solutions of a two-step type have been employed for about forty years. A two-step type permanent wave solution comprises a first solution which practically contains ammonium thioglycolate as a main component, to which a caustic alkali or an alkali carbonate is added, and a second solution which is practically an aqueous solution of alkali bromate. According to the widely believed waving theory, permanent waving is carried out in the following manner: by applying the first solution to hair, the sulfur bond (—S—S—) of cystine contained in keratin which constitutes hair is cut off (—S—H H—S—) by means of hydrogenation, thereby softening the hair into a condition wherein it is curled or strained, and then by applying the second solution to the hair, the cut off bond is recovered by oxidation (—S—H H—S—+O$_2$→—S—S—+H$_2$O) so as to fix the curls in the hair. Since a conventional permanent wave solution comprises a first solution which contains alkali (alkali carbonate, caustic alkali, or ammonia) to such an excessive degree that the first solution has alkalinity (i.e. the quantity, in terms of ml., of 0.1N-HCl which is required for neutralizing 1 ml. of the relevant alkali) of more than 3.5, when hair is coated with the first solution, a cyanide (e.g. potassium cyanide) is immediately produced. The cyanide acts to cut off the sulfur bond (—S—S—) of cystine. More specifically, a reaction between cystine (R—S—S—R, R representing keratine) and potassium cyanide (KCN) occurs in two steps as shown in the following chemical formulas (i) and (ii):

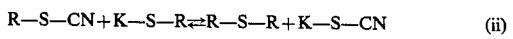

As shown above, lanthionine R—S—R and potassium thiocyanide are produced by this reaction ["CHEMICAL AND PHYSICAL BEHAVIOR OF HUMAN HAIR" by C. R. Robbins, Page 56, published by Fragrance Journal in 1982]. Then, as shown in the following chemical formula (iii), thiocyanate (—SCN) is oxidized with oxidizing agent, a main component of the second solution, alkali bromate, if the second solution is used, or by red prussiate (ferricyanide) which is a by-product in the waste liquid of the permanent wave solution even if the second solution is not used. As a result of the oxidation, cyanides are produced.

Meanwhile, lanthionine R—S—R remains in the hair, and when lanthionine is fixed, the hair is supposed to be permanently waved.

After various studies, the inventor has found it quite erroneous to consider, as in the conventional waving theory, that permanent waving is carried out by cutting off the sulfur bond of cystine by means of hydrogenation with a mercaptan, and by recovering the cut off sulfur bond by means of oxidation thereof. Instead, the inventor has found it correct to consider that permanent waving is carried out, on application of the conventional two-step type wave solution, in the steps expressed by the above chemical formulas (i) to (iii), cutting off the sulfur bond with the cyanide and recovery of the cut off sulfur bond by means of oxidation.

As stated above, cyanides are produced, when the first solution is applied to the hair, due to decomposition of keratine by the mercaptan which is the main component of the first solution and the alkali. Cyanides themselves are, as widely known, strong poisons, and further, they react with iron in hair to form hexacyano ferrous- or ferric- compounds (yellow or red prussiates), which further react with iron ions in the blood to become more poisonous than the cyanides, thus causing not only damaged hair and falling hair, but also anemia and cancer, and having a harmful effect on pregnant women (or embryos). Further, thiocyanate remaining in the hair can react with water when the hair is shampooed to produce cyanides, thus causing decomposition of hair and a short duration of the permanent waving effect of only one to two months, while leaving the hair damaged and removed of curls.

The above finding of the biochemical facts by the inventor is the basis of the presently proposed invention concerning the improved permanent wave solution.

The inventor has made studies in order to achieve permanent waving which is capable of producing the waving effect with ease, and also of improving the durability of permanently waved curls, and has already proposed a one-step permanent wave solution as well as a method of preparing an improved one-step wave solution, as disclosed in Japanese Pat. No. 730927 and U.S. Pat. No. 4,192,863.

The improved one-step permanent wave solution prepared by the method which the inventor previously proposed has the following chemical composition (in weight %):

ammonium thioglycolate: 2 to 5%;
caustic potash or caustic soda: not more than 0.1%;
oxy-organic acid: 0.1 to 0.5%;
ethyl alcohol: 0.01 to 30%
28% ammonia water: not more than 2.4%;
monoethanolamine, diethanolamine, or triethanolamine: 0.005 to 1.0%; and
distilled water as the remainder,
pH of said solution being adjusted to 7.0 to 9.6.

The improved one-step permanent wave solution can be used in beauty parlors as follows:

(1) The hair is wound on a plurality of rods and fastened with rubber bands while coating the wound hair with 50 ml. of the permanent wave solution in about 20 minutes;

(2) The head of the user is covered with a cap for about 10 to 20 minutes, and then the cap is removed; and (3) The hair as wound is rinsed with warm water, and after a lapse of a few minutes, the rods are removed from the hair. The setting is then completed by combing the hair under using a hand dryer while taking advantage of residual moisture in the hair. If desired, all or a part of the hair may be re-wound on rollers having relatively larger diameters (e.g. 1 to 2 cm) than the rods, and then dried by applying thereto hot air of about 50° to 60° C. for about 15 minutes, so as to produce large curls. Even after washing, the large curls maintain substantially to the same diameters as those of the rollers.

According to the findings of the inventor, by using the above one-step permanent wave solution, permanent waving is carried out by a combination of hydrolysis of the sulfur bond of cystine (—S—S—+H$_2$O—S—OH H—S—) and subsequent recovering of the sulfur bond by means of dehydration.

In conducting permanent waving, curtailment of the overall time required and improvement in durability of the waving effect are the things that should be pursued consistently. Further, in applying permanent wave solutions, it is an important problem to eliminate the poisonous effect of cyanides and hexacyano ferrous or ferric compounds.

SUMMARY OF THE INVENTION

Accordingly, it is the object of the present invention to provide a one-step permanent wave solution which is capable of solving the above-mentioned problems in a basically chemical manner, and also of further curtailing the overall time required for permanent waving, and which provides curls with durability which is improved to a significant extent.

To this end, the one-step permanent wave solution according to the invention has been achieved by the inventor by adjusting the chemical composition of the above-mentioned one-step permanent wave solution previously proposed by the inventor in the following manner: thioglycolic acid has been selected as a substitute for the ammonium thioglycolate, the thioglycolic acid content having been limited to a range of 2.5–3.5% in lieu of the previous range of 2–5%; the content of caustic alkali has been limited to a range of 0.045–0.075%, preferably within a precisely controlled range of 0.06–0.07%, in lieu of the previous range of not more than 0.1%; the content of the monoethanolamine, diethanolamine or triethanolamine has been limited to a range of 0.03–0.06% in lieu of the previous range of 0.005–1.0%; the content of oxy-organic acid (typically, citric acid or tartaric acid) has been limited to a lower range of 0.1–0.2% in lieu of the previous range of 0.1–0.5%; the content of 28% ammonia water has been limited to a range of 1.0–4.0% in lieu of the previous range of not more than 2.4%; and the content of ethyl alcohol has been limited to a preferable range of 0.6–3.0% in lieu of the previous range of 0.01–30%.

That is, the one-step permanent wave solution of the invention consists of (by weight):
  thioglycolic acid: 2.5 to 3.5%;
  28% ammonia water: 1.0 to 4.0%;
  caustic soda or caustic potash: 0.045 to 0.075%, preferably 0.06 to 0.07%;
  monoethanolamine, diethanolamine, or triethanolamine: 0.03 to 0.06%;
  tartaric acid or citric acid: 0.1 to 0.2%;
  ethyl alcohol: 0.6 to 3.0%; and
  distilled water: the remainder,
alkalinity of the above solution being adjusted to not more than 3.0, preferably within a range of 1.0 to 2.5.

DETAILED EXPLANATION OF PREFERRED EMBODIMENTS

The permanent wave solution according to the invention may further contain arbitrarily selected additives such as perfumes and coloring materials provided that the additives do not act counter to the objects which can be achieved by the solution.

The permanent wave solution of the invention may be used by a method substantially similar to that of the conventional one-step type permanent wave solutions.

However, in the case of the wave solution of the invention, the period required for covering the user's head with a cap can be as short as 10 minutes. The waving effect can be improved if the hair is warmed up during the covering period by applying warm air of about 40° C. on the exterior of the cap for 7 to 8 minutes, or by using a steamer or an infrared radiator. Then, the hair as wound on rods is rinsed, and after a lapse of a few minutes, the rods are removed from the hair, and the hair is rinsed again. By thus applying the permanent wave solution of the invention, any user's hair can be permanently waved safely and without damage.

Conventional permanent wave solutions, either of the one-step type or of the two-step type, contain such a large amount of alkali that the solutions have alkalinity as high as 3.5 to 7, sometimes up to 6 to 7. This is because it has been quite erroneously considered that swelling of the hair is essential and effective in order to obtain cutting off of the sulfur bond of cystine by means of reduction and recovery of the same by means of oxidation.

The high alkalinity preference based upon this erroneous consideration also appears in Japanese standards for permanent wave solutions. For instance, Notification No. 280 of the Japanese Ministry of Health and Welfare, dated June 10, 1968, requires a one-step permanent wave solution to have alkalinity, i.e. the quantity (in terms of ml.) of 0.1N-HCl required for neutralizing 1 ml. of the solution, that is within the range of 3.5 to 4.6.

In order to meet this requirement, a one-step permanent wave solution would have to contain, for instance, caustic alkali in an amount not less than 0.08 weight %, and also ammonia water in a corresponding amount. The intention to increase the alkalinity solely by using ammonia water can result in damage to the tips of the hair, and a strong smell of ammonia, thus being impractical. If alkali carbonate is used instead of ammonia, this can result in formation of cyanides, as hereinbefore described. If the content of organic amine is increased with the intention of substituting for the ammonia, this can result in a decline in the quality of the waving effect.

The inventor has made various studies in order to prevent these disadvantages, and got a novel knowledge that it is not at all necessary for the permanent wave solution to contain alkali in such a large amount as outlined above, though the solution should contain alkali in a smaller amount of as little as 0.045 to 0.075% by weight, preferably 0.06 to 0.07% by weight, which corresponds to the solution having an alkalinity of not more than 3.0. The present inventor has also found that the waving effect can be clearly improved in the latter case.

Therefore, in the wave solution according to the invention, the upper limit of the content range of the caustic alkali has been set to a value of 0.075% by weight which is lower than the lower limit of the previous content range which was 0.08%, and also the alkalinity of the solution has been reduced to a level of not more than 3.0. The preferable range of the alkalinity which is 1.0 to 2.5 has been determined by the inventor, as mentioned above, after conducting a lot of experiments and based upon the finding that by thus limiting the alkalinity of the solution, it is possible to obtain optimum results with respect to the waving effect, as well as to ensure a significantly long duration of permanently waved curls by not decomposing cystine of the hair. The content of each of the components to be used has been limited to the range mentioned above, so that the best results can be obtained in terms of a combination of the contents.

Thioglycolic acid has been selected as a substitute for the conventionally used ammonium thioglycolate, because the former of a high purity can be obtained more easily than the latter, and therefore, the content of the former can be more easily controlled to the narrow range specified above.

The permanent wave solution of the invention can be handled with ease. Therefore, the solution can be handled by anyone, while safely obtaining remarkably long-lasting curls. In fact, one of the most important characteristics of the invention is that the permanent wave solution of the invention has been found to be capable of significantly improving the durability of the permanently waved curls, thereby providing permanently waved curls which will last as long as six months. A duration of curls as long as six months has never been achieved by conventional permanent wave solutions.

This advantageous effect whereby long duration of curls is provided can be further improved by slight warming up (to about 40° C.) the hair for about 7 to 8 minutes, during a period of 10 minutes when the head of the user is covered with a cap. If the hair is thus slightly warmed up with warm air, any user's hair can be permanently curled and it is thereby possible to curtail the overall time required for permanent waving by 10 to 20 minutes. In contrast to the present invention, when using conventional permanent wave solutions which have high alkalinity, since the quality of hair and head skin can be damaged by alkali even without the hair being warmed, warming up of the hair must be avoided in order to prevent any further damage. On the other hand, the permanent wave solution according to the present invention has a level of alkalinity which is far below those of the conventional solutions and is therefore capable of providing permanently waved curls in accordance with the new waving theory without causing damage of the hair quality and the head skin. Therefore, by using the permanent wave solution according to the invention, intrinsic permanently waved curls which are glossy and which will last for about six months can be obtained by anyone with ease and safety.

According to the invention, permanent waving can be effectively achieved without causing formation of cyanides which are, as mentioned above, strongly poisonous pollutants. This characteristic of the invention offers the merits of not only to greatly improve the working environment of workers at beauty parlors but also to prevent the risk of the pollutants harming customers or those whose hair is to be permanently waved. The effect of the permanent waving according to the present invention is so remarkable that the same curl of hair can be achieved by using the rods of a diameter 2 mm greater than the conventional rods. Further, since the permanent wave solution of the invention contains alcohol, it is possible to suitably remove thiocyanates which are produced from residues of conventional permanent wave solutions and remain on the surface of hair, by the action of the alcohol, thus providing permanently waved hair with increased smoothness and gloss.

The permanent wave solution according to the present invention can be suitably used for so-called "iron-permanent waving". The permanent wave solution is applied to hair, and the hair is, under conditions of being capped for about ten minutes, slightly warmed for several minutes. Then, curling tongs of a temperature relatively low compared to conventional usage is applied to the hair, and the hair is rinsed. Thus, the curls of the hair given by the tongs are set. Singeing of hair by iron-permanent waving using a conventional permanent wave solution inevitably results in hardened and damaged hair. Such problems are solved when the permanent wave solution of the present invention is used.

Incidentally, as a proof of safety of the permanent wave solution of the invention, it is pointed out that a secondary effect of promoting generation of hair has been recognized in a number of cases of users whose hair has been permanently waved by using the permanent wave solution according to the invention. Thus, it has been found that the permanent wave solution according to the invention can make a remarkable contribution to the advancement of beauty culture techniques and hygiene.

EXAMPLE

Permanent wave solutions A and B according to the invention were obtained by pouring the following components in the following respective amounts (by weight parts) into pure water as the remainder, and agitating the components and the water into solutions.

| | A | B |
|---|---|---|
| 28% ammonia water | 3.7 | 3.7 |
| thioglycolic acid | 3.0 | 3.4 |
| monoethanolamine | 0.05 | 0.05 |
| caustic potash | 0.07 | 0.06 |
| tartaric acid | 0.15 | 0.15 |
| ethyl alcohol | 1.0 | 1.5 |
| pure water | the remainder | the remainder |
| alkalinity | 2.2 | 1.8 |

Hair samples which had never been subjected to permanent waving was wound on rods having a diameter of 2 mm while the hair was coated with the permanent wave solution A or the permanent wave solution B, fastened with rubber bands, and further coated with the solution A or the solution B. After 20 minutes has elapsed from the beginning of winding the hair, hair samples were wrapped with polyethylene films, and were kept in the wrapped condition for 10 minutes. During this 10 minutes, some of the hair sample members were subjected to warming up by application of warm air of 40° C. through the films for 7 to 8 minutes. After removal of the films, all the hair samples as wound were rinsed with warm water, and after a lapse of about 10 minutes, the rods were removed from the hair. The hair was then lightly wiped with towels. Then, after being naturally dried for 24 hours, the hair samples were dipped in warm water of 40° C. for 1 minute, in order to check the ratio of enlargement of the diameter of rings in the permanently waved curls.

For the purpose of comparison, permanent waving was conducted in the same manner as above using a conventional one-step type permanent waving solution having the following chemical composition, and the resulting hair sample was tested in the same manner as above.

| | |
|---|---|
| ammonium thioglycolate | 3.2 (as thioglycolate) |
| tartaric acid | 0.15 |

-continued

| | |
|---|---|
| ethyl alcohol | 1.0 |
| 28% ammonia water | 2.0 |
| monoethanolamine | 0.03 |
| caustic potash | 0.082 |
| pure water | the remainder |
| alkalinity | 3.8 |

The test results were as follows:

| | Enlargement Ratio of Ring Diameter | | |
|---|---|---|---|
| | Examples A and B | | Comparative Example |
| Conditions | 10 Minutes Covering | 8 Minutes Warming up | 10 Minutes Covering |
| Immediately after Waving | 2.4 | 2.0 | 3.0 |
| After Dipping in Warm Water Subsequent to Drying for 24 Hours | 2.6 | 2.2 | 3.3 |

The warm water dipping test conducted in the EXAMPLE is a test method established by the inventor which measures the durability of permanently waved curls with ease. More specifically, the test is conducted after drying the hair naturally for 24 hours by checking the degree of enlargement of the rings in the permanently waved curls after dipping the hair in warm water for 1 minute and then taking it out of the water, thereby estimating the durability of the permanently waved curls in the face of long time use.

Further, permanent waving experiments were conducted using permanent wave solutions according to the invention and the comparative, i.e. conventional, permanent wave solution, each having the above-mentioned chemical compositions. The experiments were this time carried out on the hair growing on heads of women, in the same manner as above. In the case of the permanent wave solutions of the invention, permanently waved curls obtained by using those solutions lasted 4 to 5 months even if the waving was conducted under the condition of covering the women's heads with caps for 10 minutes at a room temperature, wile 6 months was the effective duration when the hair was warmed up, too. On the other hand, permanently waved curls of all the women whose hair was permanently waved by using the comparative permanent solution showed durability of only about 3 months.

What is claimed is:

1. A one-step permanent wave solution consisting essentially of:
   (1) 2.5 to 3.5% weight of thioglycolic acid;
   (2) 1.0 to 4.0% by weight of 28% ammonia water;
   (3) 0.045 to 0.07% by weight of caustic soda or caustic potash;
   (4) 0.03 to 0.06% by weight of an amine selected from the group consisting of monoethanolamine, diethylethanolamine and triethanolamine;
   (5) 0.1 to 0.2% by weight of tartaric acid or citric
   (6) 0.6 to 3.0% by weight of ethyl alcohol; and
   (7) distilled water in an amount constituting the remainder of the mixture;
   wherein the alkalinity of the solution is in the range of 1.0 to 2.5, said alkalinity being measured in terms of the amount of ml of 0.1N HCl required to neutralize 1 ml of said solution.

2. A one-step permanent wave solution according to claim 1, wherein the proportions of the components are as follows:
   (1) thioglycolic acid: 3.0%
   (2) 28% ammonia water: 3.7%
   (3) caustic potash: 0.07%
   (4) monoethanolamine: 0.05%
   (5) tartaric acid: 0.15%
   (6) ethyl alcohol: 1.0%
   (7) distilled water: the remainder,
and the alkalinity of the solution is 2.2.

3. A one-step permanent wave solution according to claim 1, wherein the proportions of the components are as follows:
   (1) thioglycolic acid: 3.4%
   (2) 28% ammonia water: 3.7%
   (3) caustic potash: 0.06%
   (4) monoethanolamine: 0.05%
   (5) tartaric acid: 0.15%
   (6) ethyl alcohol: 1.5%
   (7) distilled water: the remainder,
and the alkalinity of the solution is 1.8.

* * * * *